(12) United States Patent
Liu

(10) Patent No.: US 6,533,790 B1
(45) Date of Patent: Mar. 18, 2003

(54) SELF-GUIDED PEDICAL SCREW

(75) Inventor: Baoren Liu, Beijing (CN)

(73) Assignee: Yuehuei H An, Charleston, SC (US)

( * ) Notice: Subject to any disclaimer, the term of this patent is extended or adjusted under 35 U.S.C. 154(b) by 230 days.

(21) Appl. No.: 09/626,671

(22) Filed: Jul. 27, 2000

(51) Int. Cl.[7] .............................................. A61B 17/56
(52) U.S. Cl. ........................... 606/73; 606/96; 411/386
(58) Field of Search ............................ 606/72, 73, 76, 606/96, 104; 411/386

(56) References Cited

U.S. PATENT DOCUMENTS

| | | | |
|---|---|---|---|
| 2,053,918 A | * 9/1936 | Peretzman | ................... 411/386 |
| 4,805,602 A | 2/1989 | Puno et al. | ..................... 606/72 |
| 5,178,539 A | * 1/1993 | Peltier et al. | ............... 433/173 |
| 5,312,255 A | * 5/1994 | Bauer | ......................... 433/174 |
| 5,369,431 A | 11/1994 | Puno et al. | ..................... 606/72 |
| 5,423,826 A | * 6/1995 | Coates et al. | ................. 606/96 |
| 5,785,476 A | * 7/1998 | McDonnell | ................. 411/386 |
| 5,871,486 A | * 2/1999 | Huebner et al. | ............. 606/73 |
| 6,158,938 A | * 12/2000 | Savoji | ........................ 411/386 |

OTHER PUBLICATIONS

"An Interlocking Screw for Fixation in Osteoporotic Bone" by Brodie E. McKoy and Yuehuei H. An, *Orthopedic Journal*, vol. III, Jun. 2000.

"An Injectable Cementing Screw for Fixation in Osteoporotic Bone" by Brodie E. McKoy and Yuehuei H. An, *Orthopedic Journal*, vol. III, Jun. 2000.

* cited by examiner

*Primary Examiner*—John J. Wilson
(74) *Attorney, Agent, or Firm*—Michael A Mann; Nexsen Pruet Jacobs & Pollard LLC

(57) ABSTRACT

A transpedicular screw having a round head and thin neck so that when the head encounters resistance, such as the harder cortex of a pedicle, it bends toward the softer axis of the pedical, thus avoiding violation of the pedicle cortex. The screw is inserted following the formation of a hole toward the pedical axis using a guide rod and a pin. Preferably this hole is made at an angle of approximately 35° with respect to the perpendicular and extends just to the pedical. The screw has a threaded body behind the neck and a tail formed to receive a tool that facilitates rotation of the screw into the pedical.

17 Claims, 4 Drawing Sheets

SELF-GUIDED PEDICAL SCREW

FIELD OF THE INVENTION

The invention relates generally to an apparatus for immobilization of the spine, and more particularly, to transpedicular screws.

BACKGROUND OF THE INVENTION

Various methods of spinal immobilization have been known and used during this century in the treatment of spinal instability and displacement. The preferred treatment for spinal stabilization is immobilization of the joint by surgical fusion, or arthrodesis. This method has been known since its development in 1911 by Hibbs and Albee. However, in many cases, and in particular, in cases involving fusion across the lumbosacral articulation and when there are many levels involved, pseudoarthrosis is a problem. It was discovered that immediate immobilization was necessary in order to allow a bony union to form. Early in the century, post operative external immobilization such as the use of splints and casts was the favored methods of treatment, however, as surgical techniques have become more sophisticated, various methods of internal and external fixation have been developed.

Internal fixation refers to methods of stabilization which are wholly internal to the patient and include commonly known devices such as bone plates and pins. External fixation in contrast involves at least some portion of the stabilization device which is external to the patient's body. Internal fixation is now the favored method of immobilization since the patient is allowed greater freedom with the elimination of the external portion of the device. Moreover, the possibility of infections, such as pin tract infection, is reduced.

Some of the indications treated by internal fixation of the spine include vertebral displacement and management such as kyphosis, spondylolishtesis and rotation; segmental instability, such as disc degeneration and fracture caused by disease and trauma and congenital defects; and tumor diseases.

A common problem with spinal fixation is the question of how to secure the fixation device to the spine without damaging the spinal cord. The pedicles are a favored area of attachment since they offer an area that is strong enough to hold the fixation device even when the patient suffers from osteoporosis. Since the middle 1950's, methods of fixation have utilized the pedicles. In early methods, screws were extended through the facets into the pedicles. Subsequently, posterior methods of fixation have been developed which utilize wires that extend through the spinal canal and hold a rod against the lamina (such as the Luque system) or that use pedicular screws that extend into the pedicle and secure a plate extending across several vertebral segments (such as the Steffe plate).

There are problems of fixation unique to this area of the spine such as the fact that the lumbar spine is normally lordotic and this lordosis must be preserved. In addition, indicated spinal decompression often requires a destabilization of the spine posteriorly. This may result in instability unless fusion is used, and fusion will often fail to become solid unless effective internal fixation is used. Finally, the points of sacral fixation are the weakest point of fixation.

Prior art devices for spinal fixation are discussed above as including the Steffe plate and the Luque System. A complete discussion of various internal fixation devices are included in L. Wiltse, "Internal Fixation of the Lumbar Spine", Clinical Orthopaedics and Related Research, February. 1986, No. 203, p.p. 2–219. Known implant configurations include facet screws, double distraction systems, compression distraction systems, springs, spinous process plates, wired implants and transpedicular screw and plate systems.

Common distraction and compression systems utilize a threaded rod and hooks which engage selected transverse processes of the vertebrae. Examples of such systems include the Harrington distraction system sold by Zimmer USA, Inc., the Keene system shown in U.S. Pat. No. 4,269,178 and the Lewis-Greenlaw System illustrated in U.S. Pat. No. 4,085,744. U.S. Pat. No. 3,648,691 to Lumb et al. shows the use of spinous process plates.

Wired implants are favored by some orthopedic surgeons because of the flexibility of the system. Dr. Eduardo Luque has developed a wired implant system where two L-shaped rods are secured along their long sides to the vertebral laminae by means of wires which pass through the vertebral foramina. The short legs of the rods extend across the vertebrae between the spinous process. A similar wired implant is shown in U.S. Pat. No. 4,604,995 to Stephens et al.

Transpedicular screw and plate systems rely on a screw threaded into a reamed canal or hole generally positioned perpendicular to the longitudinal axis of the spine and horizontal or parallel to the anterior/posterior plane of the vertebral body. Methyl methacrylate is sometimes used to secure the screw in the canal, particularly if osteoporosis is a problem. The screws engage a plate which has been bent to conform to the normal curvature of the spine or to the points of desired reduction. One such screw and plate system which has been used with significant success is the Steffee system. In this system, the screws are inserted first, the spine plates are then inserted over the pedicle screws and then posterior tapered nuts are screwed on. The screws are tightened bilaterally until the plate is locked between two nuts.

While the wired implants have the advantages of facilitating vertebral alignment, thus permitting the device to allow for variations in individual spines, and decreasing rigidity, this method of fixation includes the increased risk of damage to the neural structures. This risk can be countered by the use of transpedicular screws and plates.

The pedicle presents an area for fixation of sufficient size and depth, that under careful conditions, the risk of damage to the nerve chord is reduced. On the other hand, the use of plates with the screws is more rigid than the wired implants and the tension and compression of the plate on the screw can cause dislocation or even shearing of the screw. In addition, the current plate designs are bulky and leave little surface for bone grafting and they cannot be contoured to any lateral curvature of the spine.

Puno et al, in U.S. Pat. No. 4,805,602, presented a new system sharing advantages of both the wired implants and the plate. Specifically, they taught a screw and rod system that provides a rigidity which is intermediate the wired implant and the plate systems. While the screw and rod system theretofore retained the stability provided by the plate and screw system, the system of Puno et al, could be contoured to any plane.

Puno, et al, in U.S. Pat. No. 5,360,431, disclosed improvements in their device that reduced the time required to perform the spinal operation as compared to the prior invention, from hours to around an hour. Such a time saving represents a significant reduction in the risk associated with a surgical procedure. Further, their new design was believed to be easier to use because the chances of cross-threading the nut unto the anchor are reduced and the nut is more accessible for tightening. This is of particular significance in the bloody environment which obscures the spinal surgeon's access to the fixation device. The improved Puno et al device included a thin, chamfered nut to reduce bulk and yet includes a thread design to achieve sufficient compression on the rod. The anchor system presents a flush upper surface and each anchor seat is secured by a cancellous screw which cooperates through a sloped bore in the anchor seat so as to provide a limited ball and socket motion. The design of this system incorporates a method of therapy for treating a spinal indication utilizing this internal fixator.

For hollow screws that augment their holding power with an injectable cementitious fluid, in situ-setting calcium phosphate (Ca-P) cement and polymethyl methacrylate (PMMA) are used. Their ultimate pull-out strength of Ca-P cement- and PMMA-augmented bones is approximately the same.

Anterior cervical plate-screw fixation techniques were developed beginning in the 1960's for a more direct fixation, in particular, to overcome progressive posterior protruding deformity, instability, and graft dislodgement in the treatment of variable conditions of the cervical spine. Hollow titanium screws were introduced in 1986 for solving fixation problems in vertebral bodies which consisted of mainly cancellous bone with very thin cortex. These vertebra have only weak holding power and, consequently, the screws may loosen over time resulting in hardware failure. Failure rates as high as 35% have been reported.

For stronger fixation, pedical screws have been used through posterior approach. This procedure is technically challenging but promising. In a cadaveric study using two different screw insertion techniques—a "window" and a "blind" technique—both techniques exhibited a high percentage of screws that violated the pedicle. In the "window" technique, a laminotomy "window" is created to determine in advance the superior, medial, and interior borders of the pedicle. A "blind" technique uses only the body topographical landmarks and predetermined 30° medial and 20° superior trajectory was associated with a violation rate of 47%. Although the "window" technique had the violation rate to 25%, neither technique was successful an acceptable number of times. Others have reported violation rates of 65.5%, 39.6% and 10.6% for methods using surface landmarks, laminoforminotomy and computer assisted guide systems.

Thus there remains a need for a better technique or system for fixation using transpedicular screws than that taught by the prior art and, in particular, one that does not carry with it an unacceptably high cortical violation rate.

SUMMARY OF THE INVENTION

To overcome the high cortical violation rate of exiting pedical screws, a self-guided transpedicular (or anterior pedical) screw has been developed. It has been noted that the cortex is harder than the interior portion of the pedical. The present invention takes advantage of this circumstance in its design. This screw comprises four parts: a head, a neck, a body and a tail. The head, or leading part, is dull and rounded so that it does not easily penetrate through the harder material such as the cortex of the pedicle but does penetrate softer material. The neck connected to the head is thinner than the head, sufficiently thin so that it is flexible. If the head encounters resistence from an angle, the neck will bend, thus allowing the head to change direction in response to the resistance. The body is hollow and treaded as with conventional transpedicular screws and the tail is formed to receive a tool for rotation of the screw about its long axis. The surface of the head is polished to a gloss so that it slides along a surface more easily when it encounters a hard surface at an angle.

A feature of the present invention is the rounded, dull head. This feature is designed to prevent cortical violation and facilitate sliding when it encounters greater resistence. Because the cortex of the pedicle is harder than its interior, the head will "prefer" to move in the direction of less resistence. Thus, it will remain in the softer interior of the pedicle.

Another feature of the present invention is the thinner neck of the transpedicular screw. This feature works in combination with the rounded head to allow the screw to bend relatively easily when it meets resistence rather than try to bore its way through the resistence or remain straight notwithstanding the change in direction.

Other features and their advantages will be apparent to those skilled in the art of orthopedic surgery and transpedicular screws from a careful reading of the Detailed Description of Preferred Embodiments accompanied by the following drawings.

DETAILED DESCRIPTION OF A PREFERRED EMBODIMENT

The present invention is a transpedicular screw, made of a non-reactive material such as titanium. "Non-reactive" means that it does not react in the environments of use, particularly in the body or in a surgical environment.

Figure 1:
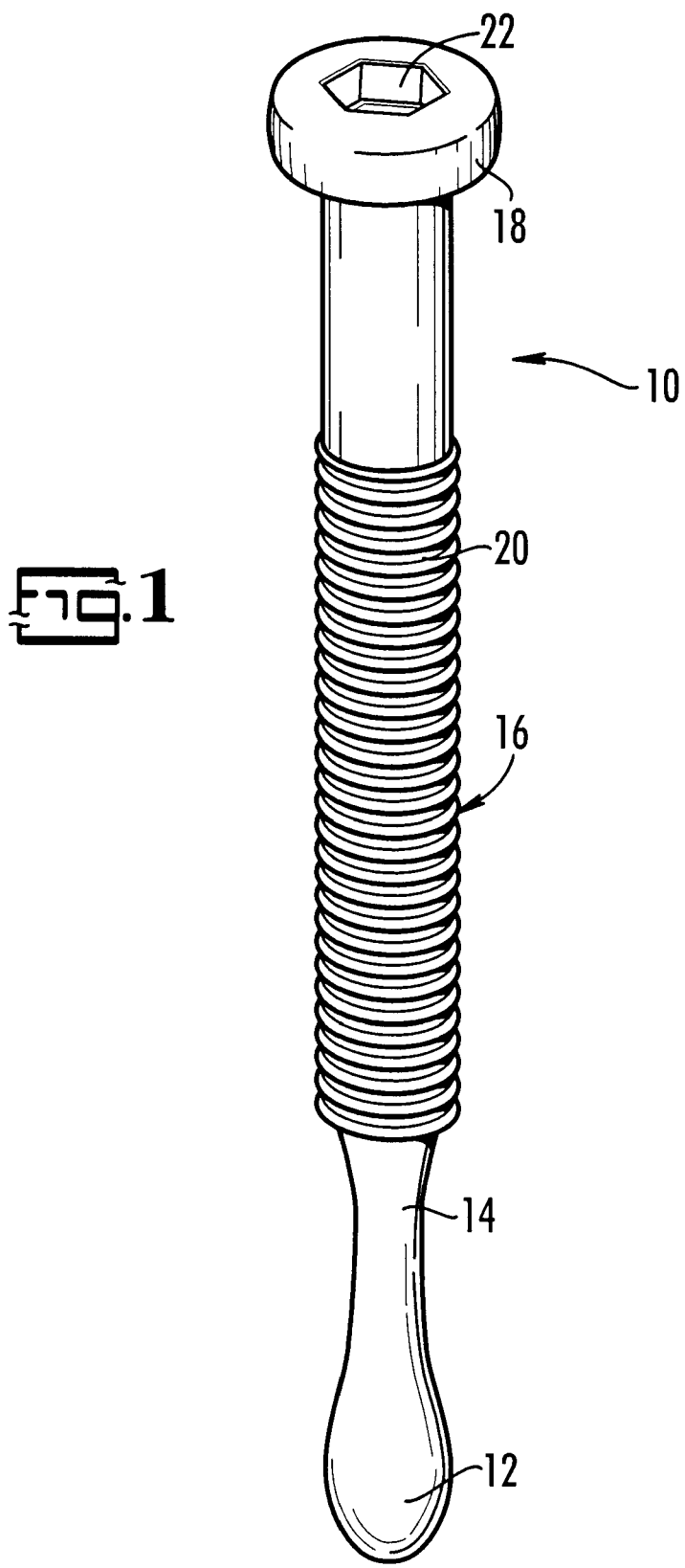
FIG. 1 is a perspective view of a transpedicular screw, according to a preferred embodiment of the present invention.

Referring now to FIG. 1, the screw, generally indicated by reference number 10 has a head 12, a neck 14 attached to head 12, a body 16 attached to neck 14, and a tail 18. Although screw 10 has these four parts, it is preferably made of a single material and all of its four parts are integrally attached. Alternatively, because these various parts have different functions, as will be explained below, different materials can be selected for each and they can then be attached in a suitably secure manner.

Head 12 is dull in the sense of "not pointed"; it is in fact rounded and polished to a shine. Preferably, it is shaped like a spindle, a tear drop or an oval ball. Most preferably, head 12 has a diameter of approximately 1.9 to 2.5 mm and a length of approximately 2.5 to 3.0 mm. Neck 14 is thinner than head 12, having a diameter of approximately 1.5 mm, and may be approximately 2.5 mm to approximately 6.0 mm in length. Importantly, neck 14 is thin enough to be flexible so that, when head 12 encounters resistence, neck 14 can be bent by the movement of head 12 away from the resistence to avoid it. Resistence in the pedicle signals that the head is approaching the cortex and departing from the pedicular axis.

Figure 3A:
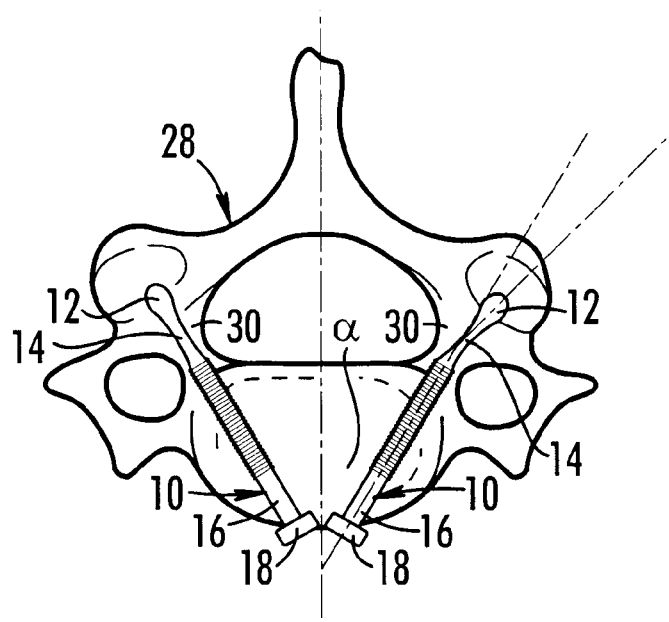
FIGS. 3A and 3B illustrate a top and side view of a lumbar vertebra with transpedicular screws inserted, according to a preferred embodiment of the present invention.
Figure 3B:
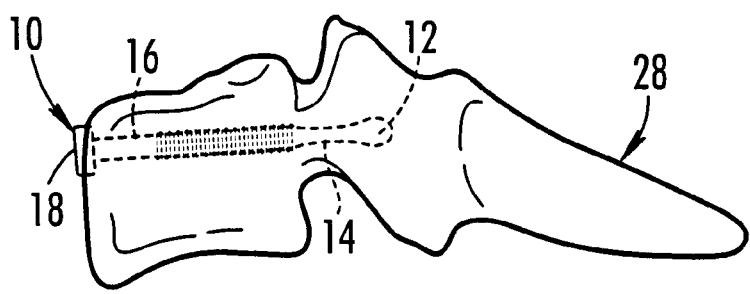
Figure 4A:
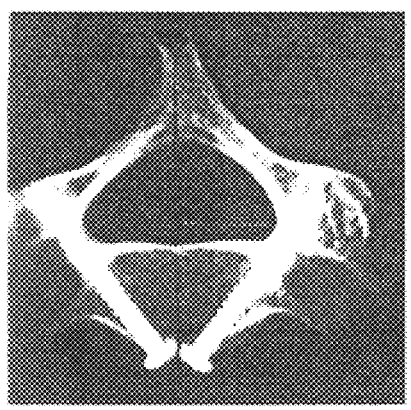
FIGS. 4A–E illustrate X-ray photographs of top views of five vertebra with transpedicular screws inserted according to a preferred embodiment of the present invention.
Figure 4B:
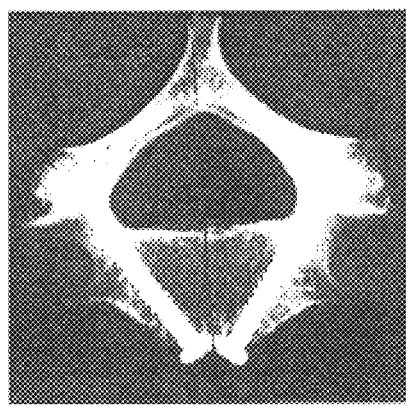
Figure 4C:
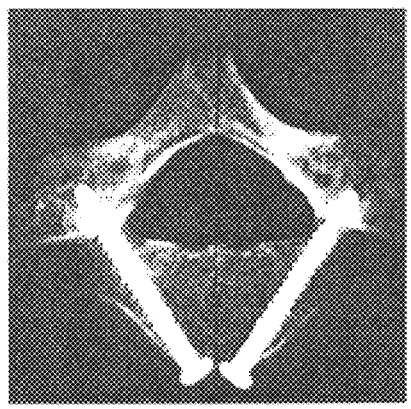
Figure 4D:
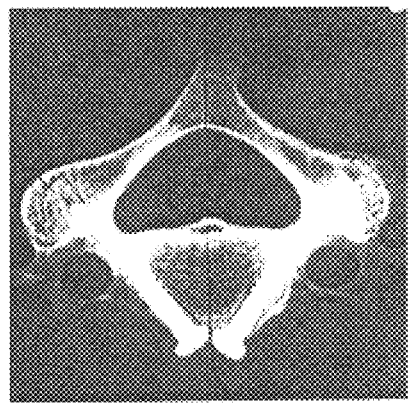
Figure 4E:
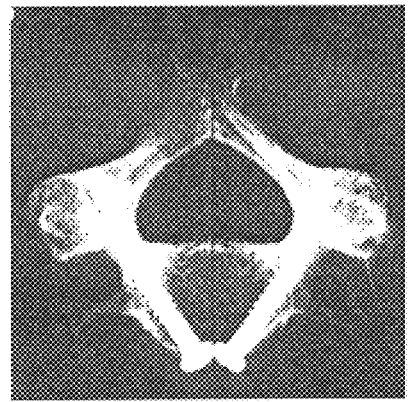

Body 16 has a series of threads 20, with an outer diameter of approximately 3.0 mm. Tail 18 has a diameter of approximately 4.5 to 5.0 mm. The overall length of screw 10 is approximately 20 to 29 mm not including tail 18, which extends from a vertebra when screw 10 is fully seated (as best seen in FIGS. 3A and 3B) and which is preferably approximately 1.5 to 2 mm long. Head 18 has a notch or recess 22 to receive a screw driver or Allen wrench.

Figure 2A:
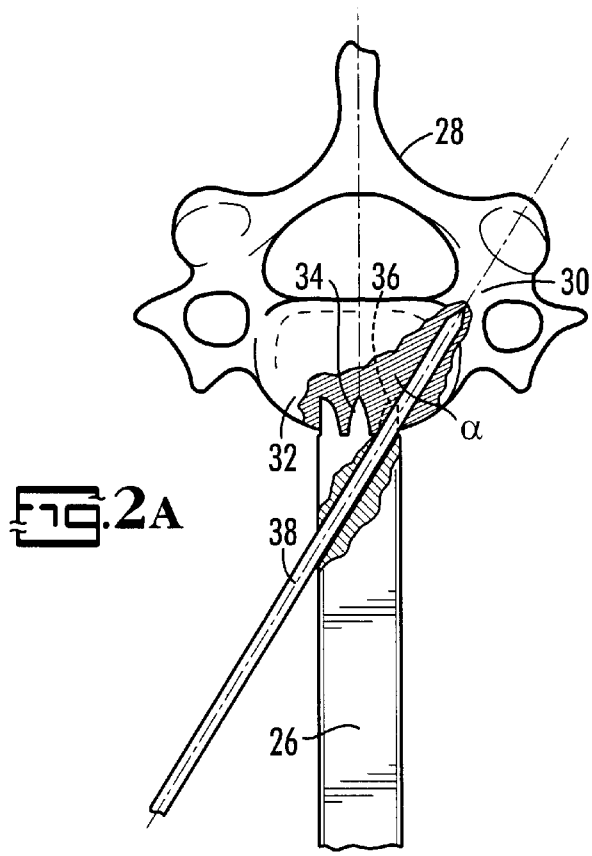
FIGS. 2A and 2B illustrate a top and a side view, respectively, of a lumbar vertebra showing a pilot hole being formed for insertion of a transpedicular screw, according to a preferred embodiment of the present invention.
Figure 2B:
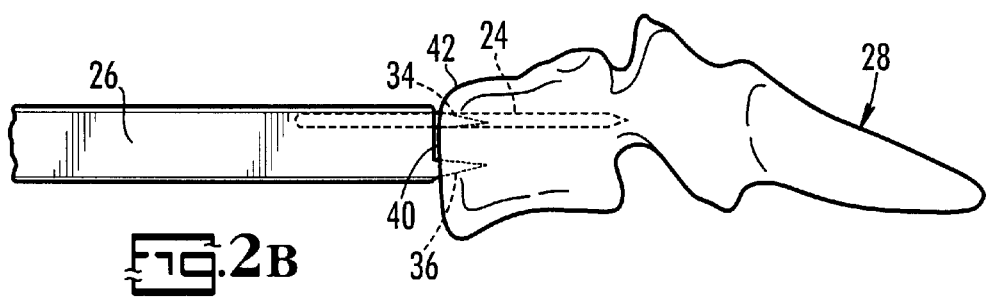

To test the effectiveness of the present transpedicular screw 10, 50 cases of flexion lateral view radiographs of the vertebra of 26 males and 24 females, aged 19–71 with an average age of 38 years, and 42 sets of X-ray films were examined for the axial direction (angle) of the pedicle, the length of the pedicle, the thickness of its narrowest portion, and the distance from the screw insertion point to the posterolateral edge of the lamina, etc., were examined to determine the best angle for insertion. Sixty of the present screw 10 were then driven into the 60 pedicles of 30 vertebra of the lower cervical spine (C3–C7) using a specially designed guide 26 (best seen in FIGS. 2 and 3). The angle of guide 26 (FIGS. 2A and 2B) for a pilot hole 24 formed in a vertebra 28 having a pedicle 30 is based on the axial direction (angle) of pedicle 30, a lateral angulation of approximately 35°, which is the same angle as the suggested medical angulation for posterior insertion of conventional pedical screws. This angle is the best estimated guide angle, BEGA, or α (FIGS. 2A and B and 3A and B). According to the X-ray measurements, there was no truly best angle for all pedicular axes at different levels. However, because of the self-guiding characteristics obtained by the dull, round head 12 and the flexible neck 14, screw 10 can automatically reorient itself along the axial line of the pedicle.

As shown in FIG. 2, three shallow drill holes 32, 34, 36, are made for anchoring guide 26. With guide 26 in place (oriented vertical to the anterior surface of the vertebral body), pilot hole 24 can then be formed in the direction of the axis of pedical 30 using a smooth pointed pin 38. Then a second guide (not shown) mirror symmetric to guide 26 is used for making the second pilot hole toward the other pedical 30. A screw driver or Allen wrench is used to insert pedical screw 10 into each pilot hole 24.

According to X-ray evaluations, angle a is confirmed at 35° lateral angulation measured vertical to the anterior surface of the vertebral body. Therefore, guide 26 for initial pilot hole 24 are made with a flat surface which will be in contact with the anterior vertebral surface 40. The level of the starting point of pilot hole 24, is estimated to be 1.5 to 2.0 mm below the anteriosuperior edge 42 or boarder of vertebra 28.

The results showed that 57 screws 10, 95%, were inserted through pedicals of cadaveric vertebra successfully. With the use of guides to obtain the best estimated guide angle, even when screw 10 is not well liked up with the axis of the pedical screw 10 can still guide itself to advance accurately within the pedical by bending its neck 14. When head 12 of screw 10 encounters the central axis of pedicle 28, it will continue to advance without bending at neck 14. If however pilot hole 24 deviates by as much as several degrees from the central axis of pedicle 28, screw 10 will bend to follow the central axis. Only three screw insertions failed because the sclerotic changes of the pedicle closed down the pedicle.

Several examples of these vertebra with the present pedical screw 10 inserted in them are illustrated in FIGS. 4A–4E. Note the left pedical screw of FIG. 4D, which is bent to avoid violating the pedical cortex.

Once in place, screw 10 will be held in place with a plate, a rod, or other device (not shown).

In the foregoing description, screw 10 has been described as being used from an anterior approach; however, it will be clear that screw 10 can also be used in a posterior approach. Finally, the present screw 10 can also be adapted for use in thoracic and lumbar vertebra.

It will be apparent to those skilled in the art of orthopedic surgery and in transpedicular screws in particular that many changes and substitutions can be made to the foregoing preferred embodiment without departing from the spirit and scope of the present invention, defined by the appended claims.

What is claimed is:

1. A screw for use in orthopedic surgery, comprising:
   a threaded body having a first end and a second end;
   a tail attached to said first end of said body, said tail having means formed thereon for receiving a tool to rotate said body; and
   avoiding means carried by said second end of said body for changing direction of said second end in response to resistance encountered during installation of said screw thus avoiding said resistance, wherein said avoiding means bends with respect to said body when encountering resistance.

2. The screw as recited in claim 1, wherein said avoiding means further comprises a head and a neck, said neck being attached to said body and said head.

3. The screw as recited in claim 2, wherein said neck is thinner in diameter than said head.

4. The screw as recited in claim 2, wherein said head is rounded.

5. The screw as recited in claim 2, wherein said head is polished.

6. The screw as recited in claim 2, wherein said neck is flexible.

7. A transpedicular screw, comprising:
   a rounded head;
   a neck narrower than said head and attached thereto, and wherein said neck is flexible;
   a threaded body having a first end and a second end, said second end attached to said neck; and
   a tail attached to said first end of said threaded body, said tail being formed to receive a tool to rotate said body.

8. The transpedicular screw as recited in claim 7, wherein said head and said neck are integrally attached.

9. The transpedicular screw as recited in claim 7, wherein said head is polished.

10. The transpedicular screw as recited in claim 7, wherein said head is approximately 1.9 to 2.5 mm in diameter and approximately 2.5 to 3.0 mm in length.

11. The transpedicular screw as recited in claim 7, wherein said neck is approximately 2.5 to 6.0 mm in length.

12. The transpedicular screw as recited in claim 7, wherein said neck is approximately 1.5 mm in diameter and said screw is hollow and made of titanium.

13. A screw apparatus for use in orthopedic surgery, comprising:
   a threaded body having a first end and a second end;
   a tail attached to said first end of said body, said tail having means formed thereon for receiving a tool to rotate said threaded body;

avoiding means carried by said second end of said threaded body for changing direction of said second end in response to resistance encountered during installation of said screw thus avoiding said resistance, said avoiding means including a head and an adjacent neck, and wherein said neck has a smaller diameter than said head; and installation assistance means in cooperation with said body, said installation assistance means being a guide having a hole formed therein and a pin dimensioned to be inserted through said hole in said guide.

14. The screw apparatus as recited in claim 13, wherein said head is rounded.

15. The screw apparatus as recited in claim 13, wherein said hole in said guide is oriented so that, when said guide is placed against a vertebra and said pin is pushed through said hole, said pin is oriented toward a pedicle of said vertebra.

16. The screw apparatus as recited in claim 13, wherein said guide carries means thereon for orienting said guide against a vertebra.

17. The screw apparatus as recited in claim 13, further comprising a tool and wherein said tail has means formed thereon for receiving said tool, said tool being adapted for rotating said screw.

* * * * *